United States Patent [19]

Marinak et al.

[11] Patent Number: 4,515,953
[45] Date of Patent: May 7, 1985

[54] PRODUCTION OF POLYCHLORINATED PYRIDINE MIXTURES BY LIQUID PHASE CHLORINATION OF PYRIDINE OR PYRIDINE HYDROCHLORIDE

[75] Inventors: Michael J. Marinak, Kelso; John L. Simonson, Longview, both of Wash.

[73] Assignee: Kalama Chemical, Inc., Kalama, Wash.

[21] Appl. No.: 487,751

[22] Filed: Apr. 22, 1983

[51] Int. Cl.³ .......................................... C07D 213/61
[52] U.S. Cl. .................................................... 546/345
[58] Field of Search .......................................... 546/345

[56] References Cited

U.S. PATENT DOCUMENTS

| | | | |
|---|---|---|---|
| 2,809,971 | 10/1957 | Bernstein et al. | 546/345 |
| 3,159,640 | 12/1964 | McClure et al. | 546/345 |
| 3,732,230 | 5/1973 | Brewer et al. | 546/345 |
| 4,108,856 | 8/1978 | Bowden et al. | 546/345 |
| 4,256,894 | 3/1981 | Dietsche et al. | 546/345 |
| 4,258,194 | 3/1981 | Weis et al. | 546/345 |
| 4,259,495 | 3/1981 | Weis | 546/345 |
| 4,275,212 | 6/1981 | Orvik | 546/345 |
| 4,287,347 | 9/1981 | Fah et al. | 546/345 |

OTHER PUBLICATIONS

Boudakian et al., Chemical Abstracts, 67: 108539e (1967).
Johnston, Chemical Abstracts, 75: 5727a (1971).
Kawamura et al., Chemical Abstracts, 84: 4814a, 164626u, 4815b, 164624s, 164625t (1976).
Wielgat et al., Chemical Abstracts, 87: 201333f (1977).
Strelkov et al., Chemical Abstracts, 91: 5120c (1979).

Primary Examiner—Henry R. Jiles
Assistant Examiner—Robert C. Whittenbaugh
Attorney, Agent, or Firm—Graybeal & Cullom

[57] ABSTRACT

Preparation of high yields of mixtures rich in polychlorinated pyridines by maintaining a chlorine to pyridine weight ratio of greater than about 4:1 when reacting chlorine and pyridine or pyridine hydrochloride non-catalytically in the liquid phase at temperatures in excess of about 150° C., the reactants being contained in a well mixed diluent producing 1 mole or less of hydrogen chloride per mole of diluent by reaction with the chlorine in the indicated temperature range. Reaction in a primary reactor is followed by selective further chlorination to obtain desired final products useful as intermediates in the formation of herbicides and the like.

38 Claims, 1 Drawing Figure

PRODUCTION OF POLYCHLORINATED PYRIDINE MIXTURES BY LIQUID PHASE CHLORINATION OF PYRIDINE OR PYRIDINE HYDROCHLORIDE

BACKGROUND OF THE INVENTION

1. Field of the Invention

The present invention relates to preparation of polychlorinated pyridine mixtures by direct liquid phase chlorination of pyridine or pyridine hydrochloride. Typical of the products produced are 2-chloro-, 3-chloro-, 2,6-dichloro-, 3,5-dichloro, 2,3,5-trichloro, 2,3,6-trichloro-, 3,4,5-trichloro, 2,3,4,5-tetrachloro-, 2,3,5,6-tetrachloro- and 2,3,4,5,6-pentachloropyridine. These products have utility, for example, as intermediates for herbicides and insecticides. A further aspect of the present invention relates to the separation of these mixed chloropyridines and then further chlorination to yield valuable higher chlorinated pyridines such as 2,6-dichloro-, 2,3,5-trichloro-, 2,3,6-trichloro-, and 2,3,5,6-tetrachloropyridine.

2. Description of the Prior Art

The utility of 2-chloropyridine as an intermediate to fungicidal and bactericidal compositions is described by Bernstein et al U.S. Pat. No. 2,809,971 and by McClure et al U.S. Pat. No. 3,159,640. In Orvik U.S. Pat. No. 4,275,212 and Fah et al U.S. Pat. No. 4,287,347, the utility of 2,3,5-trichloropyridine is described as an intermediate for herbicidal compositions. Bowden et al U.S. Pat. No. 4,108,856 describe a vapor phase chlorination process for producing 2,3,5-trichloropyridine from 3,5-dichloropyridine. 2,6-dichloropyridine is catalytically chlorinated in the liquid phase at greater than 180° C. to yield the valuable insecticidal intermediate 2,3,5,6-tetrachloropyridine in Smith et al U.S. Pat. No. 3,538,100.

The conversion of 2,3,6-trichloropyridine to 2,3,5,6-tetrachloropyridine by liquid phase ferric chloride catalyzed chlorination is taught by Dietsche et al U.S. Pat. No. 4,256,894.

Weis et al U.S. Pat. No. 4,258,194 describe a process for producing 2,3,5-trichloropyridine from 2,3,4,5-tetrachloropyridine. The valuable insecticidal intermediate 2,3,5,6-tetrachloropyridine is produced from 2,3,4,5,6-pentachloropyridine in a process described by Weis U.S. Pat. No. 4,259,495.

Brewer et al U.S. Pat. No. 3,732,230 describes a liquid phase chlorination of pyridine hydrochloride at temperatures from about 130° C. to about 175° C. with greater than 30 psig hydrogen chloride partial pressure in the reactor. The chief reaction products are 2,3,4,5-tetrachloropyridine, 2,3,5- and 3,4,5-trichloropyridine, small amounts of 3,5-dichloropyridine and a dimer polymer of pyridine.

SUMMARY OF THE INVENTION

It has been discovered that high yields of mixtures rich in chlorinated pyridines may be achieved by non-catalytically chlorinating pyridine or pyridine hydrochloride in a diluent in the liquid phase at temperatures of at least about 150° C. to about 250° C. or 260° C. while maintaining strong agitation and a feed ratio of chlorine to pyridine of at least about 4:1 by weight while feeding the chlorine and pyridine or pyridine hydrochloride to the reaction mass in a primary reactor. The pyridine can be dissolved in carbon tetrachloride or fed full strength into the reactor. It is desirable to have a supply of carbon tetrachloride available for flushing the feed line in the event of a shutdown because stagnant pyridine would otherwise tend to degrade in the feed line. If pyridine hydrochloride is the desired feed form, it is fed directly through a sparger into the bottom of the primary reactor. After the pyridine or pyridine hydrochloride has been partially chlorinated in the primary reactor, the polychloro pyridine is subjected to further chlorination in another reactor for such times and temperatures as appropriate to maximize the yield of the desired end product or products.

The percent of volatiles realized by liquid phase chlorination according to the present invention is dependent upon the diluent composition, the extent of mixing of the reactants and diluent, the pyridine feed rate to reaction mass volume, the weight ratio of chlorine-to-pyridine being fed, and the chlorine partial pressure, which influences chlorine solubility. The composition of the diluent media in which the reaction proceeds is important in practice of this invention, to secure good yields of the desired volatile chlorinated pyridines. Its function in this invention is quite different from the initiator charge described in Taplin U.S. Pat. No. 3,424,754, which deals with alpha-picoline liquid phase chlorination. In U.S. Pat. No. 3,424,754, the initiator charge has the function of evolving HCl when contacted with chlorine at the reaction temperature in order to react with alpha-picoline to form picoline hydrochloride. In the present invention, the diluent's function is to be reactively less competitive for the chlorine dissolved in it and to help remove the heat of reaction evolved by the chlorination of the pyridine.

Examples of some compounds usable as diluents in practice of the present invention, in that they generate one mole or less of HCl per mole of compound when contacted with chlorine under the reaction conditions of the present invention, are: 3-chloro-, 5-chloro-, 6-chloro-, 5,6-dichloro-, 3,5-dichloro-, 3,6-dichloro-, 3,4,5-trichloro- and 3,5,6-trichloro-2-trichloromethyl pyridine, 2-chloro-, 6-chloro-, 2,6-dichloro-3-trichloromethyl pyridine, and 2,3,6-trichloro-, 2,3,5,6-tetrachloro- and 2,3,4,5,6-pentachloro pyridine, and mixtures thereof. This list is not meant to be exhaustive of all possible diluent constituents but is illustrative of compounds useful for the purpose. The diluent may be the chlorinated pyridine/picoline products from a previous reaction which meet the above criteria and is high in volatiles content.

In practice of the present invention, an excess of chlorine is fed relative to that needed for the pyridine and pyridine hydrochloride chlorination, which excess provides additional agitation and hence better mixing, and also a higher chlorine partial pressure which increases the chlorine solubility in the reaction media. A chlorine to pyridine weight ratio of at least about 4:1 is needed. As the temperature increases in excess of 200° C., the weight ratio of chlorine to pyridine fed needs to be higher in order to achieve the high yields of the desired volatile chloro-pyridines. This is necessary because chlorine reacts more rapidly with the pyridine or pyridine hydrochloride as the temperature increases and therefore the chlorine dissolved in the reaction medium must be more rapidly replaced. This is accomplished by increasing the rate of chlorine addition relative to the pyridine flow rate which increases the chlorine partial pressure and hence its mole fraction in the liquid reaction medium. Gas solubilities tend to decrease with rising temperature, but an increase in system pressure also increases the chlorine solubility. The chlorine partial pressure in the vapor space over the reaction mass should be greater than 50% of the total pressure.

The pyridine or pyridine hydrochloride feed is to be controlled relative to the reaction volume so no more than about 10% by volume of light phase accumulates relative to the chlorinated pyridine phase at temperatures in excess of about 150° C. Potential decomposition products can result above this temperature in the absence of cooling and excess chlorine. Since pyridine hydrochloride and the diluent are somewhat immiscible and of different densities, good mixing is necessary in order to achieve dispersion of chlorine and pyridine or pyridine hydrochloride into the diluent.

Controlling these variables results in high yields of volatile polychlorinated pyridines in the liquid phase at temperatures in excess of 150° C.

Care must be taken to ensure metallic impurities such as iron, copper, aluminum and other Lewis Acid type metals are excluded from the reaction mass, as they will cause different reactions in the chlorination that may not be desirable.

DESCRIPTION OF THE PREFERRED EMBODIMENTS

EXAMPLE 1

Figure 1:
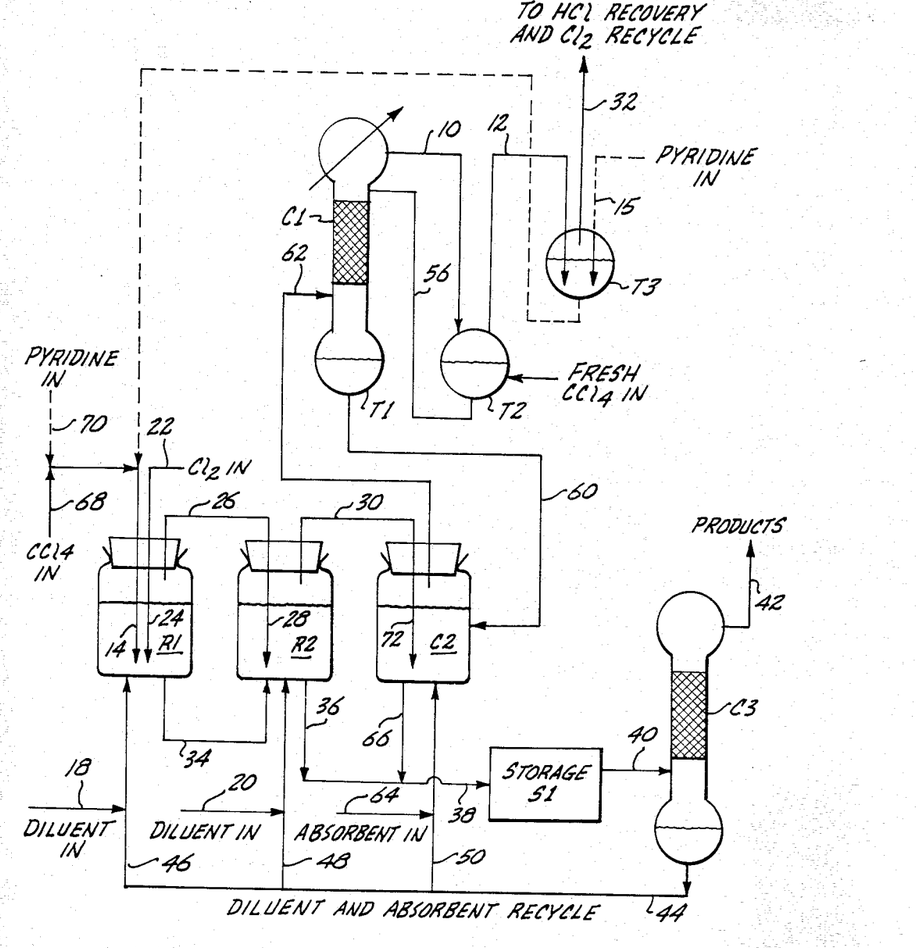
The FIGURE is a schematic diagram of a reaction system for practicing the process of the present invention on a continuous batch basis.

The FIGURE schematically illustrates a continuous batch type reaction system for producing mixtures rich in polychlorinated pyridines according to the present invention. Primary reactor R1, secondary reactor R2, and absorber C2 are suitably glass of cylindrical configuration, electrically heated and each about 1 liter in volume, and with an inside diameter of 4 inches and an inside height of 7 inches. Water cooled scrubber column C1 is suitably of cylindrical design, 1½ inches in diameter, containing as packing some 18 inches of ¼ inch glass rings.

Scrubber column C1 includes a holding tank or reservoir T1 and the overhead vapor from column C1 is delivered through vent line 10 to disengaging tank T2 in which the carbon tetrachloride collects, with the chlorine and hydrogen chloride evolving from column C1 being delivered by vent line 12 and sparged into hydrochlorination tank T3. For startup, pyridine hydrochloride, suitably previously prepared conventionally, as by sparging anhydrous HCl into a pool of pyridine maintained between 80° C. and 100° C. until saturated with HCl, is charged to hydrochlorination tank T3 and pyridine hydrochloride is withdrawn from tank T3 and delivered to bottom discharging sparger 14 in reactor R1 through line 16. An alternate startup mode involves feeding pyridine dissolved in carbon tetrachloride through lines 68 and 70 thence into line 14, generating hydrogen chloride which is vented to hydrochlorination tank T-3. For startup, also, primary reactor R1 was charged through charge line 18 with 1200 grams of diluent, consisting of chlorinated pyridines from a previous reaction (suitably comprising about 22.4% 2-trichloromethyl pyridine, 70.0% 6-chloro-, 3.9% 5,6-dichloro-, and 2.2% 3,6-dichloro-2-trichloromethyl pyridine by weight). 600 grams of like diluent material were also charged to secondary reactor R2 through charge line 20. 450 grams of a suitable absorbent were charged through charge line 64 to absorber C2, the composition of the absorbent selected for this example being the same as that charged to R1 and R2.

The absorbent charged to C2 needs to have a melting point of less than 80° C. and substantial solubility with carbon tetrachloride. Its purpose is to absorb higher melting chlorinated pyridines, e.g. those with melting points greater than 80° C., namely, 2,6-dichloro-, 2,3,5,6-tetrachloro- and 2,3,4,5,6-pentachloro pyridine. If these higher melting point chloropyridines were allowed to enter the scrubber column C1 in substantial quantity, they would tend to plug the column packing. The refluxing carbon tetrachloride in scrubber column C1 tends to concentrate the entrained chloropyridines that enter it in the bottom tank T1 thereof, and keep the overhead vapors substantially free of chlorinated pyridines which would otherwise plug the vapor outlet 10. Some typical examples which meet the criteria of suitable absorbent materials are 6-chloro, 5,6-dichloro-, 3,6-dichloro-, 3,5-dichloro-2-trichloromethyl pyridine, and mixtures thereof.

The operational startup sequence is that of introducing the diluent to the primary and secondary reactors, then initiating chlorine flow, then heating the reactors to desired reaction temperature, then initiating the pyridine or pyridine hydrochloride flow. By this procedure the pyridine or pyridine hydrochloride only sees excess chlorine in the reactors and degradation thereof to non-volatiles is avoided. Once reactors R1 and R2 were charged, external heat was applied and the temperature of primary reactor R1 thereof was maintained at 235° C., with secondary reactor R2 being maintained at 235° C. and absorber C2 maintained at 140° C. Chlorine gas from a suitable pressurized source was delivered to the reactor R1 through feed line 22 and bottom placed sparger 24 at a flow rate of 380 grams per hour. The flow rate of pyridine dissolved in carbon tetrachloride at a volume ratio of 1:1 was sparged into reactor R1 through bottom placed sparger 14, the discharge stream of which is closely adjacent (with about ½ inch spacing) to the discharge stream of chlorine sparger 24, and was maintained at a rate equivalent to 21.8 grams pyridine per hour, amounting to a chlorine to pyridine feed ratio of about 17.4:1.

As will be understood, the pyridine fed to primary reactor R1 releases hydrogen chloride from the reaction with the chlorine. This hydrogen chloride along with excess chlorine is vented from reactor R1 through vent line 26 and sparged into the charge in secondary reactor R2 through bottom discharging sparger 28, the overhead vapor including hydrogen chloride and excess chlorine being vented from reactor R2 and delivered through line 30 to absorber C2, thence through line 62 to scrubbing column C1, thence through line 10 and line 12 to hydrochlorinating tank T3, the vapor flow from which passes through line 32 to hydrogen chloride and chlorine gas recovery means known per se, for recycling of the chlorine gas to the process and recovery of the hydrogen chloride, as desired. Once hydrogen chloride gas is being generated and is passing through the system to hydrochlorination tank T3, the pyridine feed into tank T3 through line 15 can be started if that is the desired feed mode.

Secondary reactor R2 is only partially charged with diluent at startup. This is for the reason that, as the volume of the reaction mass in reactor R1 increases in the course of the reactor, a portion of the reaction mass is moved from reactor R1 to reactor R2 (by volatilization and entrainment) through line 26 and through discharge line 34 for further chlorination in reactor R2. The temperature in secondary reactor R2 influences the degree of continued chlorination.

When the liquid volume in secondary reactor R2 increases to the point where the reactor R2 is filled to its operating level, further increase in liquid volume is taken care of by progressively discharging the excess through line 36, 38 to storage surge tank S1 from which it is discharged through discharge line 40 to vacuum distillation column C3. In addition, absorbent and entrained reaction products that have been absorbed in C2 likewise are discharged through line 66 and line 38 to storage surge tank S1. This mixture of components in storage tank S1 is also fed through line 40 to vacuum distillation column C3. The lower boiling chlorinated pyridine products from storage tank S1 are distilled in C3 and are collected and discharged overhead through line 42 for further treatment as intermediate products, final products, or for further chlorination as individual products. The absorbent and diluent materials, which are higher boiling than the chlorinated products manufactured in the reaction system, are concentrated in the bottom of distillation column C3 and are returned to the process through discharge line 44 which is connected to reactor R1 through line 46, to reactor R2 through line 48, and to absorber C2 through line 50.

Liquid discharge from holding tank T2 is delivered to scrubber column C1 through line 56 to return carbon tetrachloride to the column C1, with makeup of carbon tetrachloride from an appropriate supply if necessary, as indicated at 58. The liquid phase fraction collecting in bottom tank T1 of the scrubber column C1 is returned to absorber C2, as indicated at line 60.

Excess chlorine, hydrogen chloride, some volatile corrosive chloro-pyridine hydrochlorides, and entrained chlorinated pyridines, some of which have melting points in excess of 100° C., are transferred to secondary reactor R2 from primary reactor R1 by heated vent line 26 and bottom discharging sparger 28, with the volatile hydrochlorides being absorbed and reacted further in secondary reactor R2. These hydrochlorides are very corrosive and tend to form solids on condenser surfaces that are in the 30° C. to 100° C. temperature range, the operating temperature range of scrubber column C1 and, along with the high melting chloropyridines, would there cause a plugging problem in column C1 if passed directly from primary reactor R1 to the scrubber column C1. Their absorption and further reaction in secondary reactor R2 help eliminate such plugging problems and absorber C2 completely eliminates the high melting chloropyridines in the vent line 62 to column C1. The excess chlorine, hydrogen chloride and entrained products passing to column C1 through absorber C2 vent line 62 are there scrubbed with carbon tetrachloride discharged to column C1 through line 56. The entrained chlorinated pyridine products buildup in tank T1 and the liquid level therein is controlled by recycling the excess liquid back to absorber C2 through discharge line 60. When the level in absorber C2 reaches the operating level, processing of the excess material is begun through line 66 for removal of the high melting chloropyridine reaction products from the absorber material. These chlorinated pyridine products are removed from the absorbent material by vacuum distillation in C3. Process absorbent is then recycled back to C2 through line 44 and line 50.

The residence time in each reactor R1 and R2 varies from about 5 to about 40 hours, and the total cycle time in the reactors is about 10 to 80 hours. From the previously described feed and reaction conditions set forth in Example 1, 40.8 grams per hour of product was obtained that contained about 5.6% 3-chloro-, 31.3% 2-chloro-, 15.1% 3,5-dichloro-, 2.4% 2,3-dichloro-, 23.1% 2,6-dichloro-, 2.6% 3,4,5-trichloro-, 2.8% 2,3,6-trichloro-, 4.7% 2,3,4,5-tetrachloro-, and 10.0% 2,3,4,5,6-pentachloropyridine. The volatiles content of the reaction mass was greater than 99%. These compounds can be separated by vacuum distillation for further chlorination of the pure compounds or further processing to useful products. For example, 2-chloropyridine is easily separated by vacuum distillation and is a valuable commercial product per se without further processing.

In practice of the invention appropriate variation in residence time is determinable on a predictable basis, taking into consideration the product composition desired, and the reactor pressure and reactor temperature. In addition, the quantity of diluent recycled to the reactors may also be varied to vary the residence time. In any event, as earlier indicated, the feed rate of pyridine or pyridine hydrochloride relative to the reaction volume is to be controlled so that no greater than about 10% by volume of lighter phase (undiluted pyridine hydrochloride) exists in the reaction mass.

The gases in vent line 32 from hydrochlorination tank T3 are predominantly excess chlorine and hydrogen chloride, which stream can be separated or purified by a number of conventional techniques such as absorption of the hydrogen chloride in water, or drying the chlorine and compressing the chlorine gas for recycle, or fractional distillation.

The analysis of the reaction products obtained in Example 1 is given in the following TABLE ONE. (All of the numbers in TABLES ONE, TWO, and FOUR are % by weight.)

TABLE ONE

| Compound | Example 1 |
| --- | --- |
| 3-chloropyridine | 5.6% |
| 2-chloropyridine | 31.3 |
| 3,5-dichloropyridine | 15.1 |
| 2,3-dichloropyridine | 2.4 |
| 2,6-dichloropyridine | 23.1 |

TABLE ONE-continued

| Compound | Example 1 |
|---|---|
| 2,4,6-trichloropyridine (Cl at 2,4,6 positions) | 2.6 |
| 2,3,6-trichloropyridine (Cl at 2,3,6 positions) | 2.8 |
| 2,3,4,6-tetrachloropyridine | 4.7 |
| 2,3,4,5,6-pentachloropyridine | 10.0 |

EXAMPLES 2 THROUGH 6

Examples 2 through 6 serve to illustrate some of the process variables which can occur in practice of the present invention, and for such purpose were conducted as simplified batch processes. A chlorination reactor comprising a 1000 ml spherical glass reactor, heated by an electric heating mantle, was equipped with two sparge tubes and a line which was vented through a 5000 ml glass knockout pot to a caustic scrubber. The spargers were bottom placed and closely spaced (2 centimeters apart) and the respective feed lines to the spargers were fed through rotometers and flow controlled through respective needle valves, one being supplied from the source of chlorine gas, and the other supplied from a source of pyridine (Examples 2, 3, 4) or pyridine hydrochloride (Examples 5, 6). In each run the procedure followed was the same except for the variables investigated, namely diluent composition, temperature, chlorine-to-pyridine feed ratio, residence time, and pyridine flow rate relative to reaction mass volume.

In Example 2, which is illustrative, the reactor was charged with 760 grams of diluent, the composition of which is given in the following TABLE TWO, and chlorine feed was initiated through the chlorine sparger at the rate of 380 grams per hour and the charge heated to a temperature of 170° C. Pyridine dissolved in an equal volume of carbon tetrachloride was then sparged into the reactor at the rate of about 19.8 grams per hour for a period of 4 hours. The weight ratio of chlorine to the pyridine being fed during the reaction was about 19.2:1. The reaction process parameters are tabulated in the following TABLE THREE.

In Example 2, the gross weight of the resulting reaction product was 905 grams, indicating a net production of 145 grams of product. The product was a clear tractable fluid, with a volatiles proportion of greater than 99%, as measured by internal standard gas chromatography. The constituency of the product was as tabulated in TABLE FOUR.

As indicated, additional runs, designated Examples 3, 4, 5 and 6 involved the diluents set forth in TABLE TWO, the parameters set forth in TABLE THREE, and produced reaction products comprising the compounds set forth in TABLE FOUR.

TABLE TWO

| | DILUENT COMPOSITION | |
|---|---|---|
| Compound | Examples 2,3,4 | Examples 5,6 |
| 2,6-dichloropyridine | — | 1.2% |
| 2-chloro-6-(trichloromethyl)pyridine | 72.5% | 50.7 |
| 2,3-dichloro-6-(trichloromethyl)pyridine | 4.4 | — |
| 2,6-dichloro-3-(trichloromethyl)pyridine | 20.1 | 11.3 |
| 2,3-dichloro-6-(trichloromethyl)pyridine (alt) | 2.8 | — |
| 2,6-bis(trichloromethyl)pyridine | — | 18.1 |
| 2-chloro-3,6-bis(trichloromethyl)pyridine | — | 18.6 |

TABLE THREE

| | Ex 2 | Ex 3 | Ex 4 | Ex 5 | Ex 6 |
|---|---|---|---|---|---|
| Initial Reactor Temp | 170° C. | 190° C. | 220° C. | 210° C. | 150° C. |
| Diluent charge | 760 gms | 770 gms | 775 gms | 478 gms | 465 gms |
| Feed Form | pyridine/CCl$_4$ | pyridine/CCl$_4$ | pyridine/CCl$_4$ | pyridine hydrochloride | pyridine hydrochloride |
| Cl$_2$ Flow Rate | 380 gms/hr | 380 gms/hr | 380 gms/hr | 380 gms/hr | 380 gms/hr |
| Pyridine flow rate | 19.8 gms/hr | 30 gms/hr | 14.3 gms/hr | 25 gms/hr | 18 gms/hr |
| Cl$_2$ to Pyridine ratio (by weight) | 19:1 | 12.7:1 | 26.5:1 | 14.1:1 | 21:1 |
| Reaction Time with both Cl$_2$ and pyridine feeds | 4 hrs | 8 hrs | 4 hrs | 3.5 hrs | 6 hrs |
| Amt of product produced | 145 gms | 220 gms | 105 gms | 151 gms | 157 gms |
| Volatility of produced | 99% | 99% | 99% | 98% | 99% |

TABLE THREE-continued

|  | Ex 2 | Ex 3 | Ex 4 | Ex 5 | Ex 6 |
|---|---|---|---|---|---|
| product |  |  |  |  |  |

TABLE FOUR

| Compound | Example 2 | Example 3 | Example 4 | Example 5 | Example 6 |
|---|---|---|---|---|---|
| 2-chloropyridine | 2.0% | — | 1.1% | 18.0% | 7.9% |
| 3-chloropyridine | 18.2 | 30.2% | 52.3 | 17.2 | — |
| 2,6-dichloropyridine | 35.8 | 27.6 | 7.9 | 41.9 | 60.0 |
| 2,5-dichloropyridine | 2.9 | 9.2 | 28.7 | 2.5 | — |
| 3,5-dichloropyridine | 4.4 | 5.2 | 1.2 | — | — |
| 2,3,5-trichloropyridine | 10.9 | 11.4 | 3.5 | 4.0 | 4.4 |
| 2,3,6-trichloropyridine | 21.1 | 13.1 | 2.4 | 5.7 | 22.7 |
| 2,3,5,6-tetrachloropyridine | — | — | — | — | 2.7 |
| pentachloropyridine | 4.4 | — | 2.8 | — | — |

Examples 7 through 11 are presented to demonstrate the chemistry of additional liquid phase chlorination after separation of various components from the reactor R2 effluent, as by vacuum distillation to yield the essentially pure compounds prior to such additional chlorination.

In Example 7, 2-chloropyridine, which has utility as an intermediate for fungicidal and bactericidal compositions, upon further chlorination in the liquid phase yields as its main reaction product 2,6-dichloropyridine.

EXAMPLE 7

Fifty grams of 2-chloropyridine were chlorinated in a 250 ml spherical chlorinator with 70 grams/hr. of chlorine for 3 hours at 160° C. Of the 33% 2-chloropyridine reacted, 87% went to the 2,6-dichloropyridine. This data is presented in TABLE FIVE.

This illustrates the predominant reaction occurring in Example 7:

TABLE FIVE

| Liquid Phase Chlorination of 2-chloropyridine | | |
|---|---|---|
| Compound | Initial Molar Concentration | Molar Concentration after 3 hr @ 160° C. |
| 2-chloropyridine | 100% | 67.1% |
| 2,6-dichloropyridine |  | 0.9 |
| 2,6-dichloropyridine |  | 28.7 |
| 2,5-dichloropyridine |  | 0.9 |
| 2,3,5-trichloropyridine |  | 1.7 |
| 2,3,5,6-tetrachloropyridine |  | 0.8 |

In Example 8, 2,6-dichloropyridine is converted in high yields to 2,3,5,6-tetrachloropyridine by ferric chloride catalyzed liquid phase chlorination.

EXAMPLE 8

Fifty grams of 2,6-dichloropyridine and 2 grams of anhydrous ferric chloride were chlorinated at 190° C. in the liquid phase with 70 grams per hour of chlorine for 8.25 hours to yield a 97.6% conversion to 2,3,5,6-tetrachloropyridine. TABLE SIX lists these results.

This illustrates the reaction occurring in Example 8:

TABLE SIX

Liquid Phase Chlorination of 2,6-dichloropyridine with 4 weight % FeCl₃

| Compound | Initial Molar Concentration | Molar Concentration after 2 hrs @ 190° C. | Molar Concentration after 8.25 hrs @ 190° C. |
|---|---|---|---|
| 2,6-dichloropyridine | 100% | 51% | — |
| 2,3,6-trichloropyridine | | 49 | 1.7% |
| 2,3,5,6-tetrachloropyridine | — | | 97.6 |
| pentachloropyridine | — | | 0.6 |

EXAMPLE 9

Seventy-five grams of a mixture rich in 3-chloropyridine were chlorinated for 4 hours at 200° C. and 2 hours at 210° C. with 70 grams per hour chlorine to yield mixtures rich in 2,3,5- and 2,3,6-trichloropyridine. TABLE SEVEN lists these results:

This illustrates the reactions occurring in EXAMPLE 9:

TABLE 7

Liquid Phase Chlorination of 3-chloropyridine

| Compound | Initial Molar Concentration | Molar Concentration After 4 hrs @ 200° C. + 2 hrs @ 210° C. |
|---|---|---|
| 3-chloropyridine | 100% | — |
| 2,5-dichloropyridine | | 11.5% |

TABLE 7-continued

Liquid Phase Chlorination of 3-chloropyridine

| Compound | Initial Molar Concentration | Molar Concentration After 4 hrs @ 200° C. + 2 hrs @ 210° C. |
|---|---|---|
| 2,3-dichloropyridine | | 24.0 |
| 3,5-dichloropyridine | | 8.3 |
| 2,3,5-trichloropyridine | | 20.8 |
| 2,3,6-trichloropyridine | | 35.4 |

EXAMPLE 10

Twenty-five grams of 3,5-dichloropyridine were chlorinated with 70 grams/hr of chlorine for 8 hours at 180° C. to yield a mixture rich in 2,3,5-trichloropyridine. TABLE EIGHT lists these results.

This illustrates the predominant reaction occurring in Example 10:

TABLE EIGHT

Liquid Phase Chlorination of 3,5-dichloropyridine

| Compound | Initial Molar Concentration | Molar Concentration after 8 hrs @ 180° C. |
|---|---|---|
| 3,5-dichloropyridine | 100% | 43.5% |
| 2,3,5-trichloropyridine | | 55.2 |
| 2,3,5,6-tetrachloropyridine | | 1.3 |

EXAMPLE 11

Liquid chlorination of a mixture rich in 2,3,6-trichloropyridine catalyzed with four weight percent ferric chloride is illustrated in TABLE NINE and Example 11.

Fifty grams of a mixture rich in 2,3,6-trichloropyridine was chlorinated at 195° C. for 4¼ hours. The concentration of 2,3,6-trichloropyridine decreased from 89.4% to 1.7% while the concentration of 2,3,5,6-tetrachloropyridine increased from 4.5% to 97.6%. TABLE NINE lists the results.

This illustrates the predominant reaction occurring in Example 11:

TABLE NINE

| Compound | Initial Molar Concentration | Molar Concentration after 4.25 hrs at 195° C. + 4% FeCl₃ |
|---|---|---|
| 2,3,6-trichloropyridine | 89.4% | 1.7% |
| 2,3,5,6-tetrachloropyridine | 4.5 | 97.6 |
| 2,3,4,5,6-pentachloropyridine | | 0.6 |

It has been demonstrated that various liquid phase, uncatalyzed and catalyzed chlorinations of products obtained from vacuum distillation column C3 result in a method of producing mixtures rich in 2,3,5-trichloropyridine and/or 2,3,5,6-tetrachloropyridine, if desired. Useful chlorinated pyridines such as 2-chloropyridine may be separated out by vacuum distillation prior to their chlorination, if desired.

The main criteria for the absorbent charge in absorber C2 is that it is nonreactive at the temperature at which the absorber operates (140° C.), is a compound or mixture of compounds having a melting point less than 80° C., and is mutually soluble in carbon tetrachloride so that it doesn't plug up the scrubbing column C1, either through not melting or freezing or lack of solubilization. The absorber charge, being nonreactive, is basically a one time charge and recycled after removal of the absorbed product components, with only slight makeup from time to time. Functionally, the absorbent acts and is handled in much the same way as the carbon tetrachloride in the scrubbing column C1.

The chlorination process described in Taplin U.S. Pat. No. 3,424,754 relies on chlorine gas sparging into the liquid reaction mass to dissolve the chlorine in the reaction mass and to mix alpha-picoline hydrochloride with the initiator charge. According to Chemical Engineering Handbook, Perry, 3d Edition, page 1215 (1950), agitation produced by the degree of gas sparging involved in the process of U.S. Pat. No. 3,424,754 (estimated to be about 1.5 cubic foot per square foot minute at 200° C.) is usually too mild to move immiscible liquids with appreciable density differences into good contact with each other. In reactions according to the present invention, it is a practical necessity to maintain the reaction mass well mixed so that there is good contact and quick dispersion of the pyridine hydrochloride into the diluent at the desired reaction temperatures of greater than 150° C. because the polychlorinated pyridine diluent and the pyridine hydrochloride are immiscible and have substantially different densities (about 1.6 and about 1.2 grams per cubic centimeter, respectively), and because pyridine hydrochloride is unstable in this temperature range, i.e. the salt tends to break down to its components, namely hydrogen chloride and pyridine. If there is breakdown into the components, the hydrogen chloride is volatile and escapes through the vent system and pyridine builds up in a lighter liquid phase.

Yields of volatile chlorinated pyridines in excess of 99% and other new useful products are obtained when care is taken to ensure a high partial pressure of chlorine and sufficient mixing and quick dispersion of the pyridine or pyridine hydrochloride into a chlorine rich diluent which does not substantially compete for the available chlorine. This is accomplished by sparging chlorine (in excess of that needed for the reaction) and pyridine or pyridine hydrochloride at closely spaced locations near the bottom of the reactor means containing the polychlorinated pyridine diluent charge. The mixing required to ensure adequate contact between the liquids and gas can be achieved by high gas flow rate sparging, mechanical agitation, or a combination of both. High gas flow rates as described by Braulich, A. J.; Ch. E. Journal, Volume 11, No. 1, pp 73–79, can achieve mixing of a magnitude almost equivalent to high power input mechanical mixing. Several disadvantages are inherent in the use of high gas flow rates, however. They are:

(a) high entrainment of the reactor liquids to the scrubber column C1 where they are scrubbed with carbon tetrachloride and must be recycled to the reaction system.

(b) a large volume of chlorine gas which must be purified, dried, and recycled.

Another mode of operation to enhance mixing is to combine mechanical agitation with chlorine gas and pyridine or pyridine hydrochloride sparging to achieve the desired degree of mixing and excess chlorine. High maintenance of mechanical seals and agitators are some of the disadvantages of such a mechanical agitation system.

An increase in reactor back pressure aids in increasing the chlorine concentration in the reaction liquid. The stoichiometric amount of chlorine reacted per pound of pyridine fed is about 2:1 by weight. Chlorine in excess of the stoichiometric requirement is considered essential to ensure that the pyridine or pyridine hydrochloride does not form undesirable tars and polymers. Therefore, weight ratios of at least about 4:1 of chlorine to pyridine being fed are deemed necessary in practice of the present process.

Care must be taken not to exceed the thermal stability of the diluent system. Diluents such as 6-chloro- or 5,6-dichloro-2-trichloromethyl pyridine can decompose vigorously at temperatures greater than 260° C.

The above-described embodiments are intended to be illustrative, not restrictive. The full scope of the invention is defined by the claims, and any and all equivalents are intended to be embraced therein.

What is claimed is:

1. The process of noncatalytically chlorinating pyridine or pyridine hydrochloride in the liquid phase without substantial formation of intractable nonvolatiles, said process comprising:
   (a) establishing in a reactor means a diluent reactor charge which is made up of chlorinated pyridine and/or picoline compounds, said diluent reactor charge being essentially nonreactive with chlorine in the sense of forming one mole or less of hydrogen chloride per mole of diluent under the reaction conditions to which the reactants in the reactor means are subjected;
   (b) while maintaining the reactor charge in the liquid phase and at a temperature of about 150° C. to 260° C., sparging chlorine and pyridine or pyridine hydrochloride into the reactor charge near the bottom thereof at a chlorine-to-pyridine feed ratio of at least about 4:1 by weight and at a feed rate low enough so that any separation of the reactor charge into a second, lighter phase composed of unchlorinated pyridine hydrochloride is minimized and is in any event less than about 10% of the reactor charge by volume, the excess of chlorine being fed to the reactor charge relative to the amount of pyridine being fed thereto providing enhanced agitation of the reaction mass and sufficient chlorine to ensure that the chlorine partial pressure in the vapor space over the reaction mass is greater than 50% of the total pressure; and
   (c) continuing chlorine addition and maintaining such reaction conditions until substantial nuclear substitution of chlorine in the pyridine or pyridine hydrochloride has occurred.

2. The process of claim 1, comprising continuing chlorination in the reactor means until the reaction product comprises at least about 30% by weight 2-chloropyridine.

3. The process of claim 1, comprising continuing chlorination in the reactor means until the reaction product comprises at least about 30% by weight 3,5-dichloropyridine.

4. The process of claim 1, comprising continuing chlorination in the reactor means at a temperature of at least about 150° C., for a time to substantially quantitatively convert the pyridine present to one or more of the following compounds: 2-chloro-, 3-chloro-, 2,6-dichloro-, 3,5-dichloro-, 2,3,5-trichloro-, 3,4,5-trichloro-, 2,3,6-trichloro-, 2,3,4,5-tetrachloro-, and 2,3,4,5,6-pentachloropyridine.

5. The process of claim 1, comprising the additional step of separating the product compounds by vacuum distillation.

6. The process of claim 1, wherein the diluent charged to the reactor means is selected from the group consisting of 3-chloro-, 5-chloro-, 6-chloro-, 5,6-dichloro-, 3,5-dichloro-, 3,6-dichloro-, 3,4,5-trichloro- and 3,5,6-trichloro-2-trichloromethyl pyridine, 2-chloro-, 6-chloro-, 2-6-dichloro-3-trichloromethyl pyridine, 3,5-bis(trichloromethyl)pyridine and 2-chloro- and 2,6-dichloro-3,5-bis(trichloromethyl)pyridine, 2,3,6-trichloro-, 2,3,5,6-tetrachloro- and 2,3,4,5,6-pentachloropyridine, and mixtures thereof.

7. The process of claim 1, wherein the diluent charged to the reactor means is made up essentially of the chlorinated pyridine products from a previous reaction.

8. The process of claim 1 comprising the additional steps of:
   (c) separating 2-chloropyridine from the other chlorinated pyridine products; and
   (d) chlorinating the 2-chloropyridine in the liquid phase and at a temperature of at least about 150° C. to obtain 2,6-dichloropyridine as the main reaction product.

9. The process of claim 1 comprising the additional steps of:
   (c) separating 2,6-dichloropyridine from the other chlorinated pyridine products; and
   (d) chlorinating the 2,6-dichloropyridine in the liquid phase and at a temperature of at least about 150° C. to obtain 2,3,5,6-tetrachloropyridine as the main reaction product.

10. The process of claim 1, comprising the additional steps of:
    (c) separating 3-chloropyridine from the other chlorinated pyridine products; and
    (d) chlorinating the 3-chloropyridine in the liquid phase and at a temperature of at least about 150° C. to obtain a mixture rich in 2,3,5-trichloropyridine and 2,3,6-trichloropyridine.

11. The process of claim 1, comprising the additional steps of:
    (c) separating 3,5-dichloropyridine from the other chlorinated pyridine products; and
    (d) chlorinating the 3,5-dichloropyridine in the liquid phase and at a temperature of at least about 150° C. to obtain 2,3,5-trichloropyridine as the main reaction product.

12. The process of claim 1, comprising the additional steps of:
    (c) separating a mixture rich in 2,3,6-trichloropyridine from the other chlorinated pyridine products; and
    (d) chlorinating the 2,3,6-trichloropyridine in the liquid phase and at a temperature of at least about 150° C. to obtain 2,3,5,6-tetrachloropyridine as the main reaction product.

13. The process of noncatalytically chlorinating pyridine or pyridine hydrochloride in the liquid phase without substantial formation of intractable nonvolatiles, said process comprising:
    (a) establishing in a reactor means a diluent reactor charge which is made up of chlorinated pyridine and/or picoline compounds, said diluent reactor charge being essentially nonreactive with chlorine in the sense of forming one mole or less of hydrogen chloride per mole of diluent under the reaction conditions to which the reactants in the reactor means are subjected;
    (b) while maintaining the reactor charge in the liquid phase and at a temperature of about 150° C. to 260° C., sparging chlorine and pyridine or pyridine hydrochloride into the reactor charge near the bottom thereof at a chlorine-to-pyridine feed ratio of at least about 4:1 by weight and at a feed rate low enough so that any separation of the reactor charge into a second, lighter phase composed of unchlorinated pyridine hydrochloride is minimized and is in any event less than about 10% of the reactor charge by volume, the excess of chlorine being fed to the reactor charge relative to the amount of pyridine being fed thereto providing enhanced agitation of the reaction mass and sufficient chlorine to ensure that the chlorine partial pressure in the vapor space over the reaction mass is greater than 50% of the total pressure;
(c) continuing chlorine addition and maintaining such reaction conditions until substantial nuclear substitution of chlorine in the pyridine or pyridine hydrochloride has occurred; and
(d) continuing chlorine addition and maintaining the reaction mass in the liquid phase and at a temperature of at least about 150° C. in a second reactor until the desired extent of further nuclear substitution of chlorine in the pyridine or pyridine hydrochloride has occurred.

14. The process of claim 13, performed in a continuous batch mode and in a series of at least two reactors, with the first two reactors having initial, essentially inert diluent charges as in step (a) of claim 13, with the reaction conditions of step (b) of claim 13 being maintained in a first reactor, with excess chlorine, hydrogen chloride, and entrained products being transferred by vent line and sparger from the first reactor to the second reactor, with overflow liquid products of chlorination being transferred from the first reactor to the second reactor, and with the volatile hydrochlorides being absorbed and reacted further in the second reactor.

15. The process of claim 14, comprising continuing chlorination in the second reactor until the reaction product comprises at least about 30% by weight 2-chloropyridine.

16. The process of claim 14, comprising continuing chlorination in the second reactor until the reaction product comprises at least about 30% by weight 3,5-dichloropyridine.

17. The process of claim 14, comprising continuing chlorination in the second reactor at a temperature of at least about 150° C., for a time to substantially quantitatively convert the pyridine present to one or more of the following compounds: 2-chloro-, 3-chloro-, 2,6-dichloro-, 3,5-dichloro-, 2,3,5-trichloro-, 3,4,5-trichloro-, 2,3,6-trichloro-, 2,3,4,5-tetrachloro-, and 2,3,4,5,6-pentachloropyridine.

18. The process of claim 17, comprising the additional step of separating the product compounds of vacuum distillation.

19. The process of claim 13, wherein the diluent charged to the reactor means is selected from the group consisting of 3-chloro-, 5-chloro-, 6-chloro-, 5,6-dichloro-, 3,5-dichloro-, 3,6-dichloro-, 3,4,5-trichloro- and 3,5,6-trichloro-2-trichloromethyl pyridine, 2-chloro-, 6-chloro-, 2,6-dichloro-3-trichloromethyl pyridine, 3,5-bis(trichloromethyl)pyridine, 2-chloro- and 2,6-dichloro-3,5-bis(trichloromethyl)pyridine, 2,3,6-trichloro-, 2,3,5,6-tetrachloro- and 2,3,4,5,6-pentachloro pyridine, and mixtures thereof.

20. The process of claim 13, wherein the diluent charged to the reactor is made up essentially of the chlorinated pyridine products from a previous reaction.

21. The process of claim 13, comprising the additional steps of:
(d) separating 2-chloropyridine from the other chlorinated pyridine products; and
(e) chlorinating the 2-chloropyridine in the liquid phase and at a temperature of at least about 150° C. to obtain 2,6-dichloropyridine as the main product.

22. The process of claim 13 comprising the additional steps of:
(d) separating 2,6-dichloropyridine from the other chlorinated pyridine products; and
(e) chlorinating the 2,6-dichloropyridine in the liquid phase and at a temperature of at least about 150° C. to obtain 2,3,5,6-tetrachloropyridine as the main reaction product.

23. The process of claim 13 comprising the further steps of:
(d) separating 3-chloropyridine from the other chlorinated pyridine products; and
(e) chlorinating the 3-chloropyridine in the liquid phase and at a temperature of at least about 150° C. to obtain a mixture rich in 2,3,5-trichloropyridine and 2,3,6-trichloropyridine.

24. The process of claim 13 comprising the additional steps of:
(d) separating 3,5-dichloropyridine from the other chlorinated products; and
(e) chlorinating the 3,5-dichloropyridine in the liquid phase and at a temperature of at least about 150° C. to obtain 2,3,5-trichloropyridine as the main product.

25. The process of claim 13, comprising the additional steps of:
(d) separating a mixture rich in 2,3,6-trichloropyridine from the other chlorinated pyridine products; and
(e) chlorinating the 2,3,6-trichloropyridine in the liquid phase and at a temperature of at least about 150° C. to obtain 2,3,5,6-tetrachloropyridine as the main reaction product.

26. The process of noncatalytically chlorinating pyridine or pyridine hydrochloride in the liquid phase without substantial formation of intractable nonvolatiles, said process comprising:
(a) establishing in a reaction means a diluent reactor charge which is made up of chlorinated pyridine and/or picoline compounds, said diluent reactor charge being essentially nonreactive with chlorine in the sense of forming one mole or less of hydrogen chloride per mole of diluent under the reaction conditions to which the reactants in the reactor means are subjected;
(b) while maintaining the reactor charge in the liquid phase and at a temperature of about 150° C. to 260° C., sparging chlorine and pyridine or pyridine hydrochloride into the reactor charge near the bottom thereof at a chlorine-to-pyridine feed ratio of at least about 4:1 by weight and at a feed rate low enough so that any separation of the reactor charge into a second, lighter phase composed of unchlorinated pyridine hydrochloride is minimized and is in any event less than about 10% of the reactor charge by volume, the excess of chlorine being fed to the reactor charge relative to the amount of pyridine being fed thereto providing enhanced agitation of the reaction mass and sufficient chlorine to ensure that the chlorine partial pressure in the vapor space over the reaction mass is greater than 50% of the total pressure;
(c) continuing chlorine addition and maintaining such reaction conditions until substantial nuclear substitution of chlorine in the pyridine or pyridine hydrochloride has occurred;
(d) continuing chlorine addition and maintaining the reaction mass in the liquid phase and at a temperature of at least about 150° C. in a second reactor means until the desired extent of further nuclear substitution of chlorine in the pyridine or pyridine hydrochloride has occurred; and (e) sparging gases from the second reactor means to an absorber means containing an absorbent having a melting point of less than about 80° C. and a substantial solubility with carbon tetrachloride, such absorbent being maintained at a temperature of about 140° C. and functioning to effectively liquify and remove any higher melting point chloropyridines from the gases sparged thereto.

27. The process of claim 26, performed in a continuous batch mode and in a series of at least two reactors, with the first two reactors having initial, essentially inert diluent charges as in step (a) of claim 26, with the reaction conditions of step (b) of claim 26, being maintained in a first reactor, with excess chlorine, hydrogen chloride, and entrained products being transferred by vent line and sparger from the first reactor to the second reactor, with overflow liquid products of chlorination being transferred from the first reactor to the second reactor, and with the volatile hydrochlorides being absorbed and reacted further in the second reactor.

28. The process of claim 27, comprising continuing chlorination in the second reactor means until the reaction product comprises at least about 30% by weight 2-chloropyridine.

29. The process of claim 27, comprising continuing chlorination in the second reactor means until the reaction product comprises at least about 30% by weight 3,5-dichloropyridine.

30. The process of claim 27, comprising continuing chlorination in the second reactor means at a temperature of at least about 150° C., for a time to substantially quantitatively convert the pyridine present to one or more of the following compounds: 2-chloro-, 3-chloro-, 2,6-dichloro-, 3,5-dichloro-, 2,3,5-trichloro-, 3,4,5-trichloro-, 2,3,6-trichloro-, 2,3,4,5-tetrachloro-, and 2,3,4,5,6-pentachloropyridine.

31. The process of claim 30, comprising the additional step of separating the product compounds by vacuum distillation.

32. The process of claim 27, wherein the diluent charged to the reactor means is selected from the group consisting of 3-chloro-, 5-chloro-, 6-chloro-, 5,6-dichloro-, 3,5-dichloro-, 3,6-dichloro-, 3,4,5-trichloro- and 3,5,6-trichloro-2-trichloromethyl pyridine, 2-chloro-, 6-chloro-, 2,6-dichloro-3-trichloromethyl pyridine, 3,5-bis(trichloromethyl)pyridine, 2-chloro- and 2,6-dichloro-3,5-bis(trichloromethyl)pyridine, 2,3,6-trichloro-, 2,3,5,6-tetrachloro- and 2,3,4,5,6-pentachloro pyridine, and mixtures thereof.

33. The process of claim 27, wherein the diluent charged to the reactor is made up essentially of the chlorinated pyridine products from a previous reaction.

34. The process of claim 26 comprising the additional steps of:
(e) separating 2-chloropyridine from the other chlorinated pyridine products; and
(f) chlorinating the 2-chloropyridine in the liquid phase and at a temperature of at least about 150° C. to obtain 2,6-dichloropyridine as the main product.

35. The process of claim 26 comprising the additional steps of:
(e) separating 2,6-dichloropyridine from the other chlorinated pyridine products; and
(f) chlorinating the 2,6-dichloropyridine in the liquid phase and at a temperature of at least about 150° C. to obtain 2,3,5,6-tetrachloropyridine as the main reaction product.

36. The process of claim 26, comprising the additional steps of:
(e) separating 3-chloropyridine from the other chlorinated pyridine products; and
(f) chlorinating the 3-chloropyridine in the liquid phase and at a temperature of at least about 150° C. to obtain a mixture rich in 2,3,5-trichloropyridine and 2,3,6-trichloropyridine.

37. The process of claim 26, comprising the additional steps of:
(e) separating 3,5-dichloropyridine from the other chlorinated pyridine products; and
(f) chlorinating the 3,5-dichloropyridine in the liquid phase and at a temperature of at least about 150° C. to obtain 2,3,5-trichloropyridine as the main product.

38. The process of claim 26, comprising the additional steps of:
(e) separating a mixture rich in 2,3,6-trichloropyridine from the other chlorinated pyridine products; and
(f) chlorinating the 2,3,6-trichloropyridine in the liquid phase and at a temperature of at least about 150° C. to obtain 2,3,5,6-tetrachloropyridine as the main reaction product.

* * * * *